US011679031B2

(12) United States Patent
Xiao

(10) Patent No.: US 11,679,031 B2
(45) Date of Patent: Jun. 20, 2023

(54) FUNDUS ALIGNMENT IN OPTICAL TREATMENT SYSTEMS

(71) Applicant: LUTRONIC VISION INC., Burlington, MA (US)

(72) Inventor: Zhen Xiao, Beijing (CN)

(73) Assignee: LUTRONIC VISION INC., Burlington, MA (US)

( * ) Notice: Subject to any disclaimer, the term of this patent is extended or adjusted under 35 U.S.C. 154(b) by 721 days.

(21) Appl. No.: 16/639,833

(22) PCT Filed: Aug. 17, 2017

(86) PCT No.: PCT/CN2017/097838
§ 371 (c)(1),
(2) Date: Feb. 18, 2020

(87) PCT Pub. No.: WO2019/033337
PCT Pub. Date: Feb. 21, 2019

(65) Prior Publication Data
US 2020/0360181 A1    Nov. 19, 2020

(51) Int. Cl.
*A61F 9/008* (2006.01)
*A61B 3/13* (2006.01)
(Continued)

(52) U.S. Cl.
CPC .......... *A61F 9/008* (2013.01); *A61B 3/13* (2013.01); *A61B 3/14* (2013.01); *G02B 27/017* (2013.01);
(Continued)

(58) Field of Classification Search
CPC ...... A61F 2009/0035; A61F 2009/0043; A61F 9/008; A61F 2009/00844;
(Continued)

(56) References Cited

U.S. PATENT DOCUMENTS 5,098,426 A * 3/1992 Sklar ................ A61F 9/008
606/4
6,921,169 B2 * 7/2005 Su ..................... A61B 3/154
351/206
(Continued)

FOREIGN PATENT DOCUMENTS

CN    1708266 A    12/2005
CN    105246426 A    1/2016
(Continued)

OTHER PUBLICATIONS

International Search Report and Written Opinion for International Application No. PCT/CN2017/097838 dated May 16, 2018, pp. 11.
(Continued)

*Primary Examiner* — Ahmed M Farah

(57) ABSTRACT a laser-based ophthalmological treatment system(200) may include a device housing(202), a head fixation assembly(206), and an interactive display device(324, 424). The head fixation assembly(206) may be configured to position and to retain a head of a patient relative to the device housing(202). The interactive display device(324,424) may be positioned in an optical path(304,404). The interactive display device(324,424) may be fixed relative to the head fixation assembly(206). The interactive display device(324,424) may be configured to display a simulation scene(504) that may include a target image(502) into a visual field of the patient. The target image(502) may be displayed in the simulation scene(504) such that optical focus on the target image(502) by the patient aligns a portion of a fundus(130) of an eye of the patient in the optical path(304,404).

9 Claims, 12 Drawing Sheets

(51) Int. Cl.
  *A61B 3/14* (2006.01)
  *G02B 27/01* (2006.01)
  *G06F 3/01* (2006.01)
  *A61F 9/00* (2006.01)

(52) U.S. Cl.
  CPC ...... *G06F 3/011* (2013.01); *A61F 2009/0043* (2013.01); *A61F 2009/00844* (2013.01); *A61F 2009/00863* (2013.01); *A61F 2009/00885* (2013.01); *G02B 2027/0174* (2013.01)

(58) Field of Classification Search
  CPC .. A61F 2009/00851; A61F 2009/00885; A61F 2009/00898; A61B 3/13; A61B 3/132; A61B 3/14; G02B 27/017; G06F 3/011
  USPC ........... 606/4–6, 10–12; 607/88–93; 128/898
  See application file for complete search history.

(56) References Cited

U.S. PATENT DOCUMENTS

| | | | | |
|---|---|---|---|---|
| 7,288,106 | B2* | 10/2007 | Heacock | A61N 5/062 606/4 |
| 11,213,427 | B2* | 1/2022 | Xiao | A61F 9/009 |
| 2006/0106438 | A1* | 5/2006 | Zemmouri | A61F 9/00821 607/89 |
| 2008/0033408 | A1* | 2/2008 | Bueler | A61F 9/00825 606/5 |
| 2015/0005750 | A1* | 1/2015 | Kelleher | A61F 9/00718 606/27 |
| 2016/0270656 | A1* | 9/2016 | Samec | A61B 3/1216 |
| 2020/0360184 | A1* | 11/2020 | Xiao | A61F 9/009 |
| 2020/0360515 | A1* | 11/2020 | Xiao | A61K 41/0028 |

FOREIGN PATENT DOCUMENTS

| | | |
|---|---|---|
| CN | 106389004 A | 2/2017 |
| WO | 2014/172641 A1 | 10/2014 |

OTHER PUBLICATIONS

Huang, F-C., et al., "The Light Field Stereoscope: Immersive Computer Graphics via Factored Near-Eye Light Field Displays with Focus Cues," ACM Transactions on Graphics, vol. 34, Issue 4, pp. 1-12 (Aug. 2015).

Li, G., et al., "Holographic display for see-through augmented reality using mirror-lens holographic optical element," Optics letters, vol. 41, Issue 11, pp. 2486-2489 (Jun. 2016).

Ozerdem, U., "A Simple Nonmydriatic Self-Retinal Imaging Procedure Using a Kowa Genesis-D Hand-Held Digital Fundus Camera," Ophthalmic Research, vol. 42, No. 3, pp. 125-127 (2009).

* cited by examiner

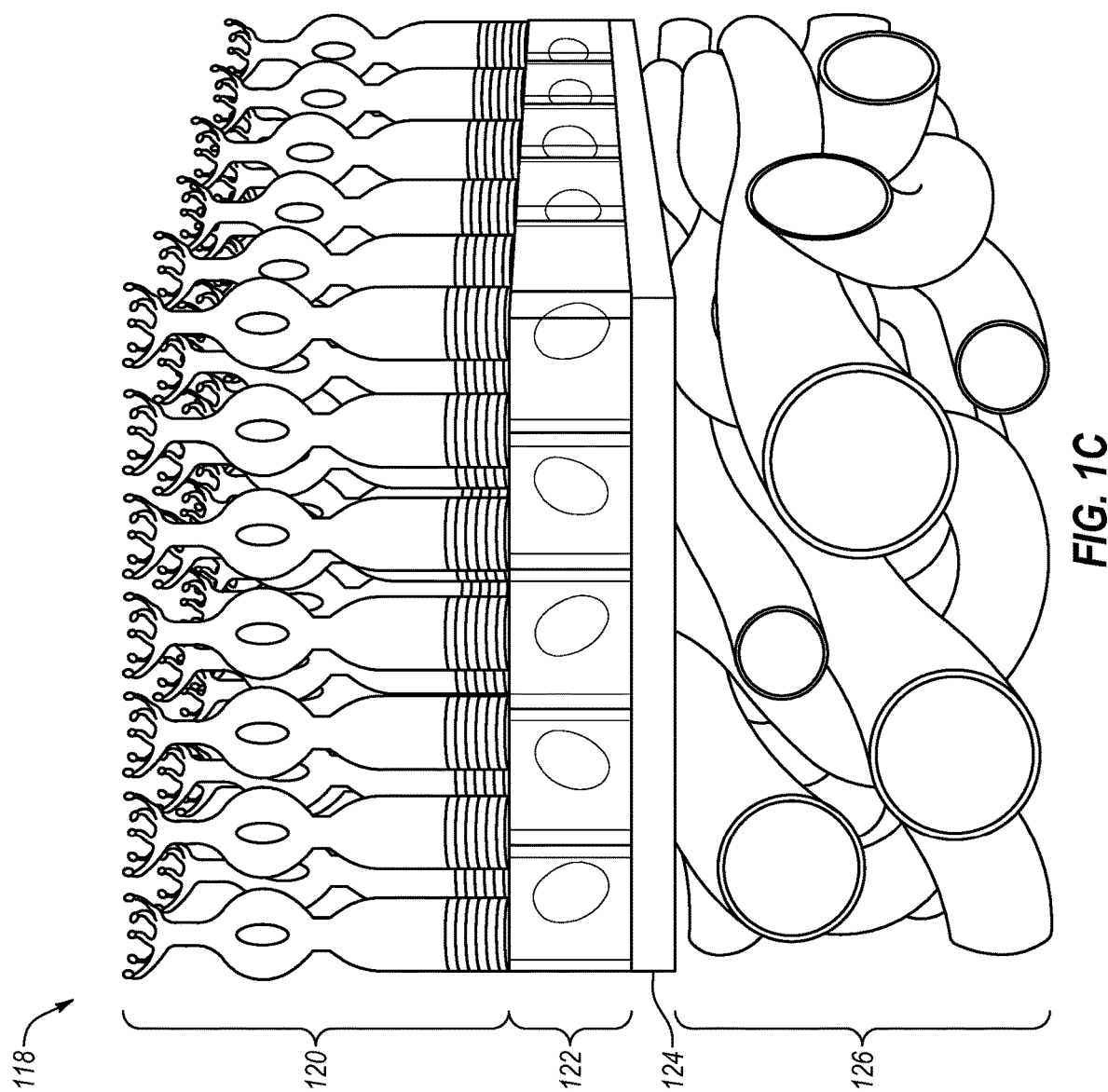

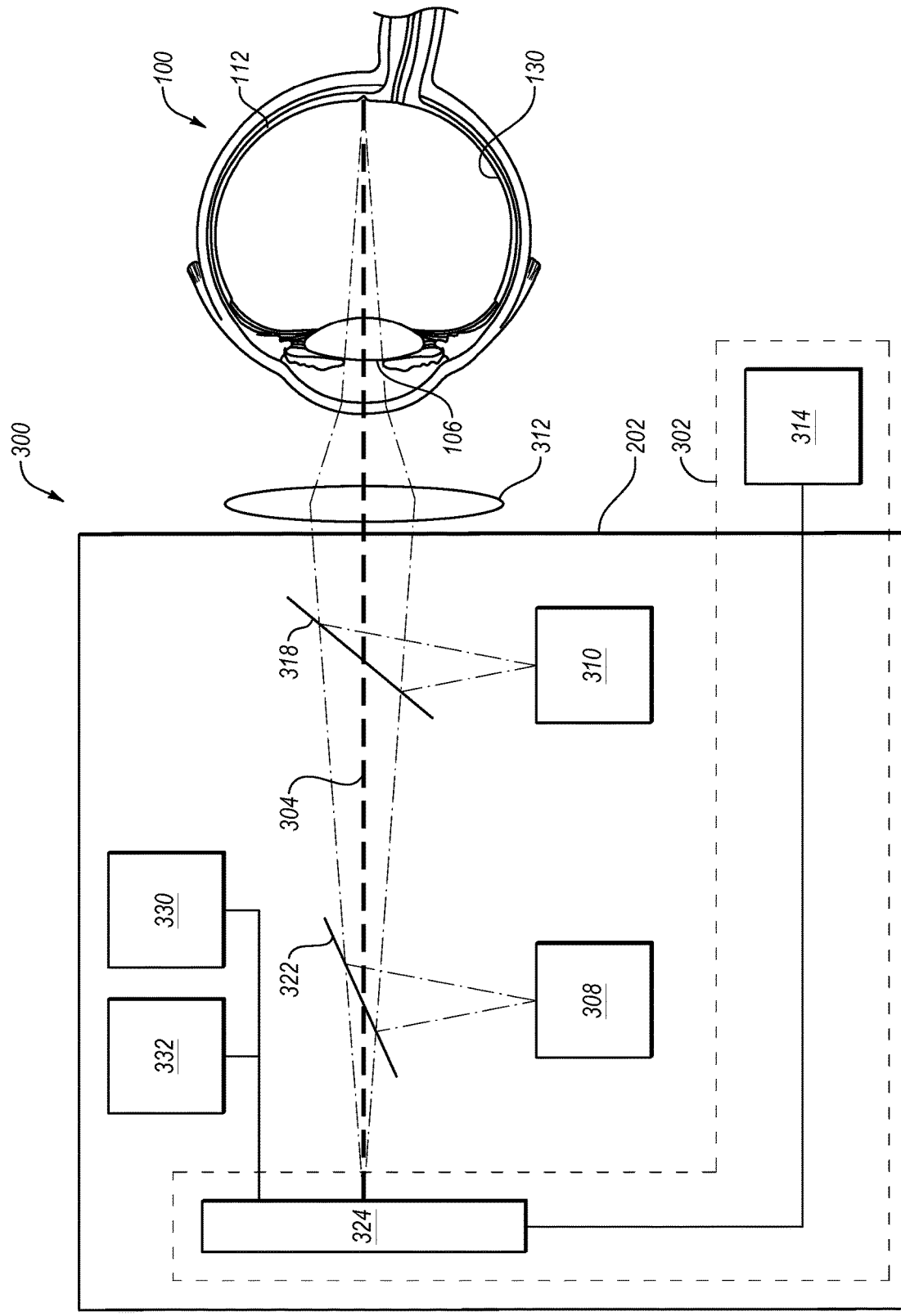

FUNDUS ALIGNMENT IN OPTICAL TREATMENT SYSTEMS

CROSS-REFERENCE

This patent application is a section 371 nationalization of PCT Application No. PCT/CN2017/097838 filed Aug. 17, 2017, which PCT application is incorporated herein by specific reference in its entirety.

BACKGROUND

Unless otherwise indicated herein, the materials described herein are not prior art to the claims in the present application and are not admitted to be prior art by inclusion in this section.

Macula disease may result in loss of vision or reduction in quality of vision of a patient. Diabetic macular edema (DME), age-related macular degeneration (AMD), and central serous chorioretinopathy (CSC) are examples of macula disease. In some circumstances, therapeutic radiation may be administered to an eye of a patient to treat the macula disease. Administration of the therapeutic radiation may involve alignment between a therapeutic radiation source and a diseased portion of a fundus. It may be difficult to perform the alignment. Accordingly, a trained healthcare provider may perform the alignment. Additionally, treatment of some macular disease may include multiple administrations of the therapeutic radiation, each of which may involve the alignment between the therapeutic radiation source and the diseased portion of the fundus.

SUMMARY

Techniques described herein generally relate to therapeutic radiation treatment systems and methods.

In an example embodiment, a laser-based ophthalmological treatment system may include a device housing, a head fixation assembly, and an interactive display device. The head fixation assembly may be configured to position and to retain a head of a patient relative to the device housing. The interactive display device may be positioned in an optical path. The interactive display device may be fixed relative to the head fixation assembly. The interactive display device may be configured to display a simulation scene that may include a target image into a visual field of the patient. The target image may be displayed in the simulation scene such that optical focus on the target image by the patient aligns a portion of a fundus of an eye of the patient in the optical path.

In another example embodiment, an interactive display device assembly may include an interactive display device and a control device. The interactive display device may be positioned in an optical path. The interactive display device may be configured to display a simulation scene that may include a target image. The target image may be displayed in the simulation scene such that optical focus on the target image by a patient aligns a portion of a fundus of an eye of the patient in the optical path. The control device may be communicatively coupled to the interactive display device. The control device may be configured to receive patient input from the patient. The interactive display device may be configured to manipulate the simulation scene in response to the patient input.

In yet another example embodiment, a method of laser-based ophthalmological surgical treatment (hereinafter, "method") may include, in a diagnostic stage, fixing a head of a patient in a head fixation assembly that is secured relative to a device housing. The method may include in the diagnostic stage, displaying to the patient a simulation scene that may include a target image within a visual field of a patient. The simulation scene may be displayed by an interactive display device fixed relative to the head fixation assembly. The method may include, in the diagnostic stage, enabling alignment of a portion of a fundus of an eye of the patient in an optical path based on optical focus by the patient on the target image. Responsive to alignment of the portion of the fundus, the method may include in the diagnostic stage acquiring a fundus image of the portion of the fundus. In a treatment stage that may be subsequent to the diagnostic stage, the method may include re-fixing the head in the head fixation assembly. The method may include, in the treatment stage, re-displaying the simulation scene to the patient. The simulation scene may include the target image as displayed in the diagnostic stage. The method may include, in the treatment stage, enabling subsequent alignment of the portion of the fundus in the optical path based on optical focus by the patient on the target image. The method may include, in the treatment stage, transmitting a pulse of laser radiation through a pupil of the patient to the portion of the fundus.

In some embodiments, a laser-based ophthalmological treatment system can include: a device housing having an optical path; a head fixation assembly configured to position and to retain a head of a patient at a fixed distance relative to the device housing with an eye of the patient aligned with the optical path; and an interactive display device positioned in the optical path. In some aspects, the interactive display device is at a fixed distance relative to the head fixation assembly. In some aspects, the interactive display device is configured to display a simulation scene that includes a target image into a visual field of the eye of the patient when aligned with the optical path. In some aspects, the interactive display device is configured to display the target image in the simulation scene such that optical focus on the target image by the patient aligns a portion of a fundus of the eye of the patient with the optical path. In some embodiments, a first optical element is in the optical path. In some aspects, the therapeutic radiation source is positioned outside of the optical path and oriented to direct the pulse of laser radiation to the first optical element. In some aspects, a second optical element is in the optical path, wherein the fundus photography device is positioned outside the optical path and oriented to capture the fundus image reflected from the optical path by the second optical element.

In some embodiments, the head fixation assembly includes: a jaw portion; a forehead rest; and
a fixing band coupled to the forehead rest.

In some embodiments, the system includes a microscope aligned with the optical path.

In some embodiments, a method of laser-based ophthalmological surgical treatment can include a diagnostic stage and a treatment stage. In some aspects, the diagnostic stage can include: fixing a head of a patient in a head fixation assembly that is secured relative to a device housing; displaying to the patient a simulation scene that includes a target image within a visual field of a patient, wherein the simulation scene is displayed by an interactive display device fixed relative to the head fixation assembly; aligning a portion of a fundus of an eye of the patient in an optical path based on optical focus by the patient on the target image; and acquiring a fundus image of the portion of the fundus during alignment of the portion of the fundus with the optical path. In some aspects, the treatment stage that is subsequent to the diagnostic stage can include: displaying the simulation scene to the patient, wherein the simulation scene includes the target image as displayed during the diagnostic stage; aligning the portion of the fundus in the optical path based on optical focus by the patient on the target image; and transmitting a pulse of laser radiation through a pupil of the patient to the portion of the fundus.

In some embodiments, the method can include: receiving patient input from a control device that is communicatively coupled to the interactive display device; manipulating one or more objects in the simulation scene in response to the patient input; and receiving a signal from a controller that indicates the patient is optically focused on the target image when a first object of the one or more objects reaches the target image. In some aspects, the method can include aligning the first object with a second object in the simulation scene by manipulating the one or more objects. In some aspects, the method can include providing an aiming reticle with the target image. In some aspects, the method can include providing the target image with a depth of field. In some aspects, the optical focus on the target image by the patient affects an elongation of a lens of the eye. In some aspects, the method includes modifying a characteristic selected from a position of the target image, a brightness of the target image, or a depth of field of the target image. In some aspects, the method includes aligning the portion of the fundus by positioning the eye straight ahead or converging inward at a particular angle.

In some embodiments, a laser-based ophthalmological treatment system can include: a device housing having an optical path; a head fixation assembly configured to position and to retain a head of a patient at a fixed distance relative to the device housing with an eye of the patient aligned with the optical path; a therapeutic radiation source positioned in the device housing and operably coupled with the optical path, wherein the therapeutic radiation source is configured to transmit a pulse of laser radiation; a camera in the device housing and operably coupled with the optical path; an interactive display device in the device housing and positioned in the optical path; a control device communicatively coupled to the interactive display device, wherein the control device is configured to receive patient input from the patient. In some aspects, the interactive display device is at a fixed distance relative to the head fixation assembly. In some aspects, the interactive display device is configured to display a simulation scene that includes a target image into a visual field of the eye of the patient when aligned with the optical path. In some aspects, the interactive display device is configured to manipulate the simulation scene in response to the patient input. In some aspects, the interactive display device is configured to display the target image in the simulation scene such that optical focus on the target image by the patient aligns a portion of a fundus of the eye of the patient with the optical path. In some aspects, the system can include a microscope aligned with the optical path.

The foregoing summary is illustrative only and is not intended to be in any way limiting. In addition to the illustrative aspects, embodiments, and features described above, further aspects, embodiments, and features will become apparent by reference to the drawings and the following detailed description.

BRIEF DESCRIPTION OF THE FIGURES

The foregoing and following information, as well as other features of this disclosure, will become more fully apparent from the following description and appended claims, taken in conjunction with the accompanying drawings. Understanding that these drawings depict only several embodiments in accordance with the disclosure and are, therefore, not to be considered limiting of its scope, the disclosure will be described with additional specificity and detail through use of the accompanying drawings.

FIG. 1C is a cross-sectional perspective view of a portion of the macula of FIG. 1B;

FIG. 3 is a block diagram of a first example subsystem of an embodiment of the system of FIGS. 2A and 2B;

DETAILED DESCRIPTION

Figure 1A:
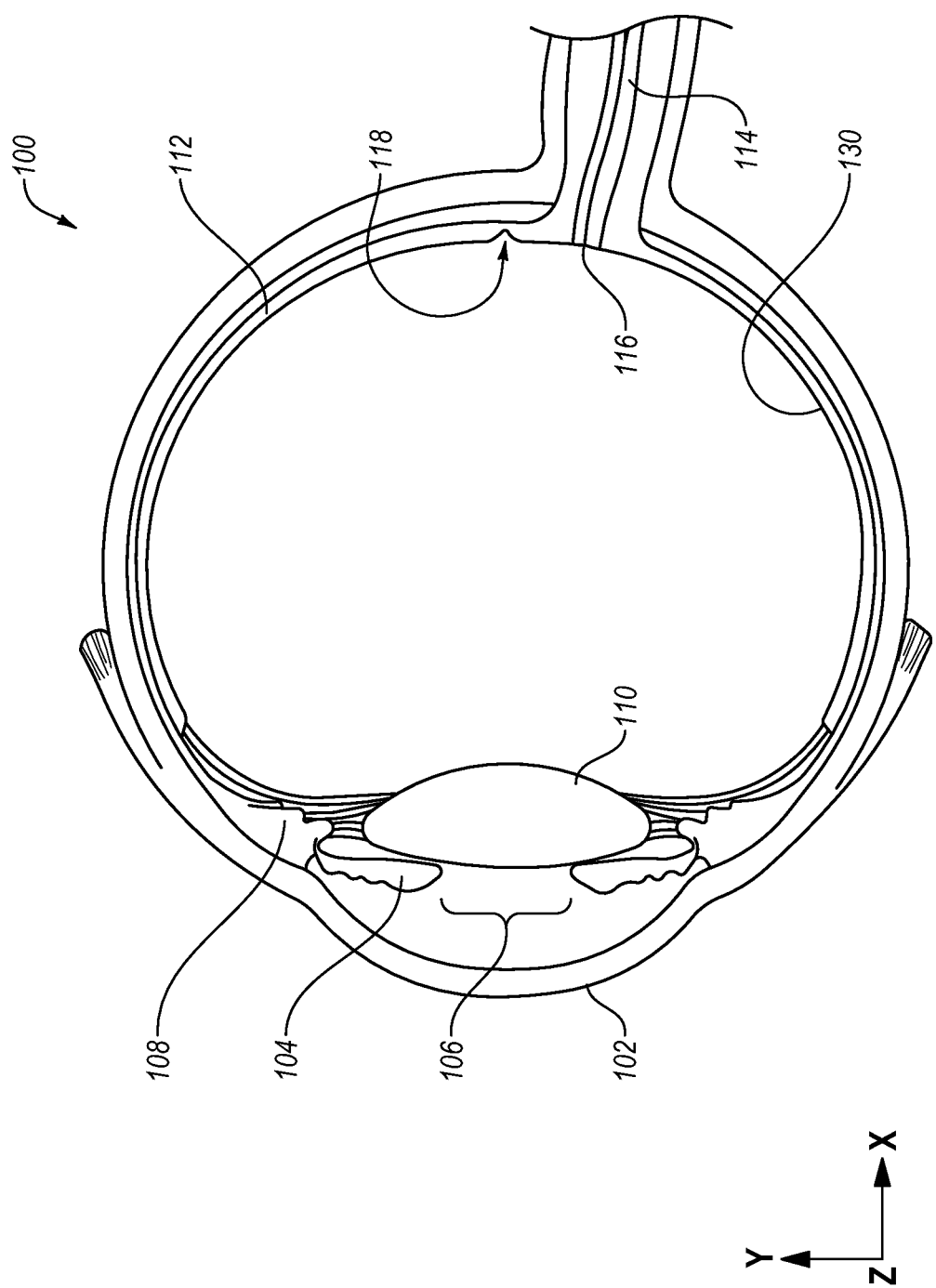
FIG. 1A is a cross-sectional view of an example human eye (hereinafter "eye")

This disclosure is generally drawn to methods, apparatus, systems, devices, and computer program products related to therapeutic radiation dosimetry.

In this detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be utilized, and other changes may be made, without departing from the spirit or scope of the subject matter presented herein. The aspects of the present disclosure, as generally described herein, and illustrated in the Figures, can be arranged, substituted, combined, separated, and designed in a wide variety of different configurations, all of which are explicitly contemplated herein.

Macula disease such as diabetic macular edema (DME), age-related macular degeneration (AMD), and central serous chorioretinopathy (CSC) may result in vision impairment or vision loss. Diagnosis and treatment of the macula disease may involve alignment of a portion of a fundus of an eye along an optical path. In some existing systems, a trained healthcare provider may perform the alignment, which may increase costs associated with treatment of the macula disease.

Accordingly, some embodiments described herein include a laser-based ophthalmological treatment system. The laser-based ophthalmological treatment system may include a device housing, a head fixation assembly, and an interactive display device. The head fixation assembly may be configured to position and to retain a head of a patient relative to the device housing. The interactive display device may be positioned in an optical path and fixed relative to the head fixation assembly. The interactive display device may be configured to display a simulation scene that may include a target image into a visual field of the patient. The target image may be displayed in the simulation scene such that optical focus on the target image by the patient aligns a portion of a fundus of an eye of the patient in the optical path. Following alignment of the portion of the fundus in the optical path, a fundus image may be acquired, which may be used to diagnosis the macula disease. Following the diagnosis, the patient may return for treatment of the macula disease. The same or substantially the same target image may display to the patient. The portion of the fundus may be re-aligned in the optical path using the target image. Thus, a process of alignment during the diagnosis and the treatment of macula disease may be simplified. For example, involvement of a trained healthcare provider may be reduced and/or a patient may be able to perform the alignment or re-alignment without the trained healthcare provider.

FIG. 1A is a cross-sectional view of an example human eye (hereinafter "eye") 100. The eye 100 may include a cornea 102, an iris 104, a pupil 106, a ciliary body 108, a lens 110, a retina 112, a fundus 130, and an optic nerve 114. The retina 112 generally includes a light-sensitive layer of tissue upon which optics of the eye 100 project an image of the visual world external to the eye 100. Through a series of chemical and electrical events, nerve impulses may be triggered in response to light striking the retina 112. The nerve impulses may be processed in vision centers of the brain such that the visual world may be perceived by a person.

The fundus 130 of the eye 100 includes an interior surface of the eye 100 opposite the lens 110. The fundus 130 may include a portion of the retina 112. The retina 112 includes an optic disc 116, sometimes referred to as the "blind spot." The retina 112 may also include a macula 118. The macula 118 may be separated from the optic disc 116 on the retina 112.

The eye 100 may rotate in a socket to view an object. Rotation of the eye 100 may orient the pupil 106 and the retina 112 to receive light from the object. The pupil 106 allows the light to enter the eye 100. When the eye 100 moves, the pupil 106 and the retina 112 may move in the y-direction and/or the z-direction of an arbitrarily defined Cartesian coordinate system of FIG. 1A. Additionally, in response to the light, a diameter of the pupil 106 may change.

The ciliary body 108 may be attached to the lens 110 via zonula fibers 132. The ciliary body 108 may change a shape of the lens 110 as the eye 100 focuses on the object within a particular depth of field. For instance, when an object is near the eye 100, the object may be out of focus or blurry. When the shape of the lens 110 changes shape, the object may appear in focus. The shape of the lens 110 may dictate how the light strikes the retina 112.

Figure 1B:
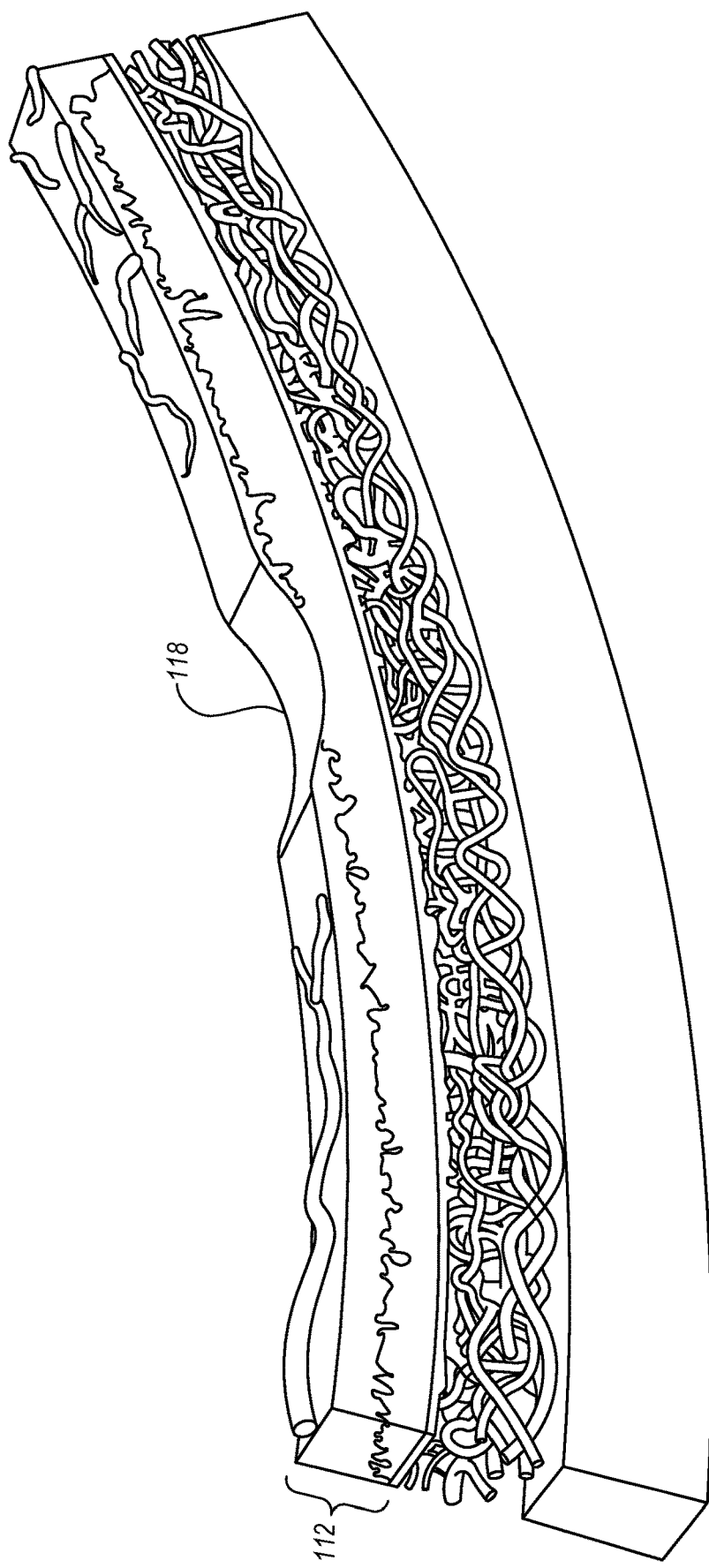
FIG. 1B is a cross-sectional perspective view of a portion of a retina and a macula of FIG. 1B.

FIG. 1B is a cross-sectional perspective view of a portion of the retina 112 and the macula 118 of FIG. 1A.

FIG. 1C is a cross-sectional perspective view of a portion of the macula 118 of FIG. 1B. FIG. 1C depicts various layers that may make up the macula 118, including photoreceptors 120, retinal pigment epithelial (RPE) cells 122, Bruch's membrane 124, and choroid 126. The macula 118 may have a relatively high concentration of photoreceptors 120 compared to the rest of the retina 112 and without blood vessels, for central and/or high-resolution vision. The RPE cells 122 may nourish the photoreceptors 120 by supplying nutrients from the choroid 126 and transporting extracellular material out through the Bruch's membrane 124.

Various conditions may adversely affect vision in the eye 100. For instance, with reference to FIGS. 1A-1C, AMD may involve degradation of the RPE cells 122 in the macula 118. In dry AMD, degraded RPE cells 122 may fail to transport extracellular material which may then begin to build up ("Drusen") in between the Bruch's membrane 124 and the RPE cells 122. The Drusen may interfere with the supply of nutrients to the photoreceptors 120, which can lead to vision loss. In wet AMD, new blood vessels (neovascularization) may grow from the choroid 126 and penetrate the Bruch's membrane 124 and the RPE cells 122 to supply nutrients to the photoreceptors 120. The new blood vessels may be weak and prone to bleeding and leakage, which may result in blood and protein leakages, which in turn may damage the photoreceptors 120 and fuel rapid vision loss.

Another condition that may adversely affect vision in the eye 100 may be DME. In more detail, persons with diabetes may experience a slowing of metabolism over time, which may reduce the ability of retinal vessels to deliver enough nutrients, which in turn may induce neovascularization. Fluid leakage from the neovascularization may cause the retina 112 to swell, causing vision loss.

Another condition that may adversely affect vision in the eye 100 may be CSC. In CSC, leakage of fluid accumulates under the central macula 118, resulting in blurred or distorted vision, which may progressively decline with each recurrence.

Some embodiments described herein include a laser-based ophthalmological surgical system that includes a therapeutic radiation source configured to emit therapeutic radiation to treat AMD, DME, CSC, and/or other conditions of the eye 100.

Figure 2A:
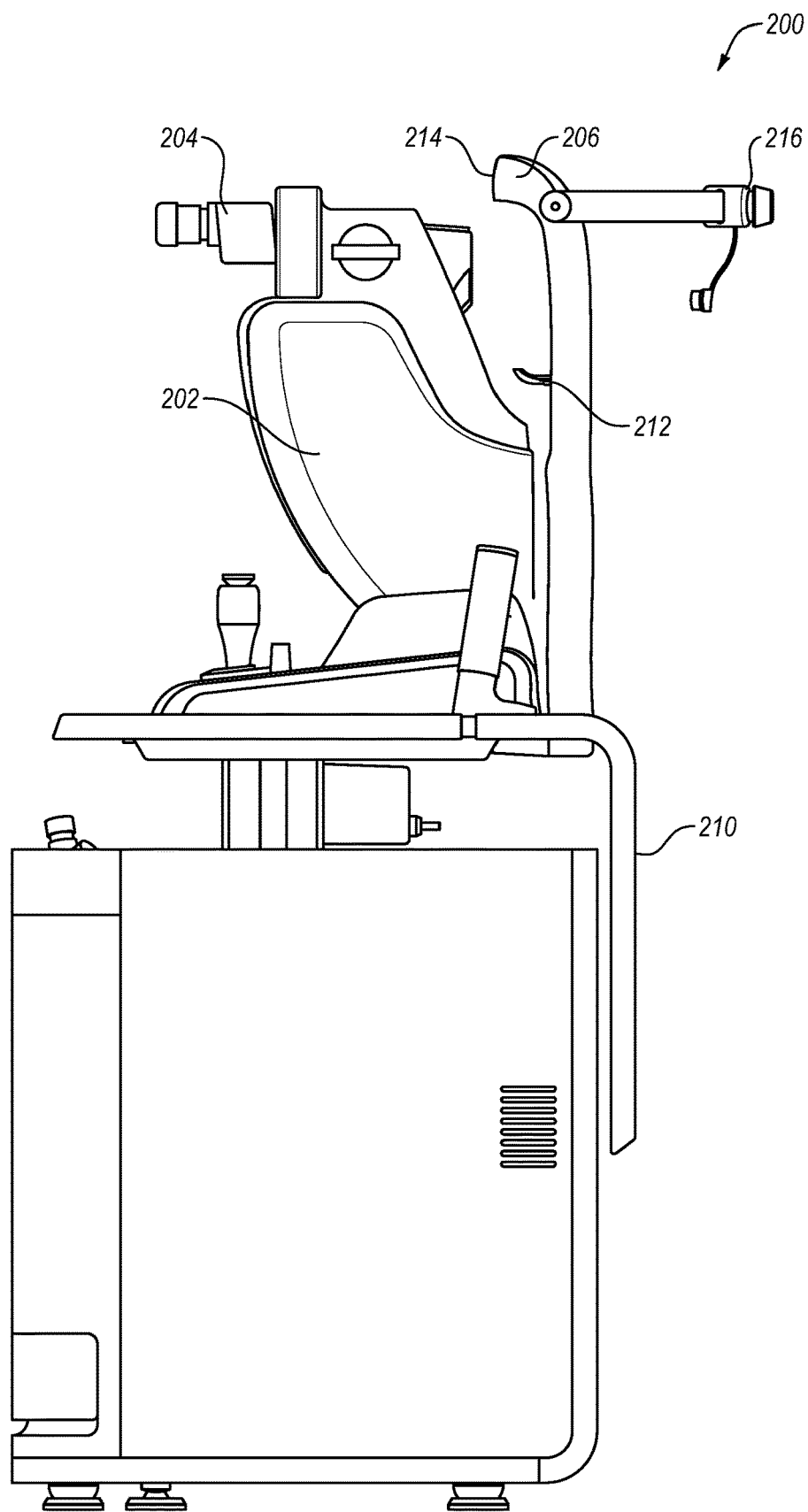
FIG. 2A illustrates an example laser-based ophthalmological surgical system (hereinafter "system")
Figure 2B:
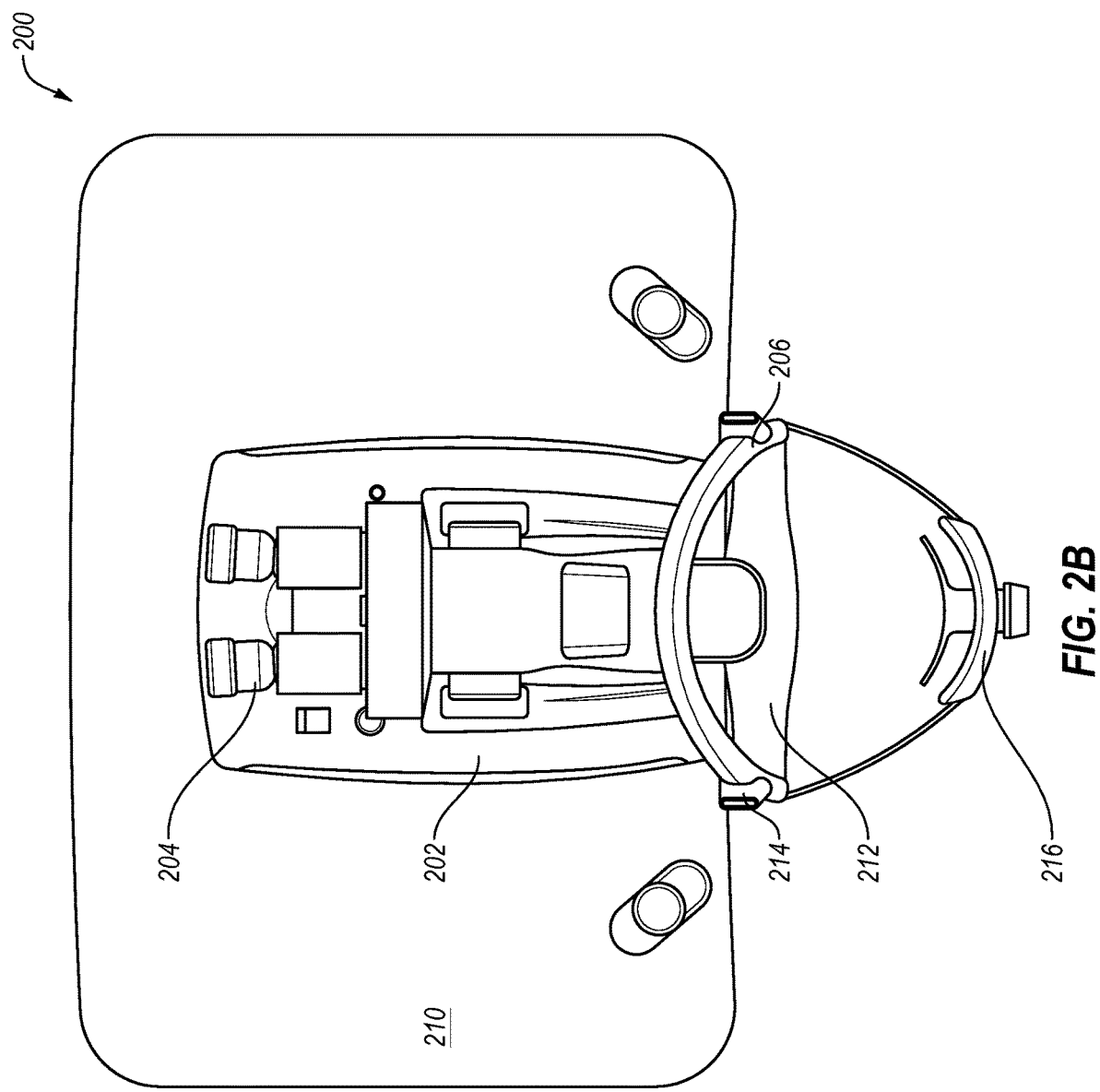
FIG. 2B illustrates another view of the system of FIG. 2A.

FIGS. 2A and 2B illustrate an example laser-based ophthalmological treatment system 200 (hereinafter, system), arranged in accordance with at least one embodiment described herein. FIG. 2A is an exterior side view of the system 200. FIG. 2B is an exterior top view of the system 200. The system 200 may be configured to administer laser-based treatment of a macular disease (e.g., AMD, DME, CSC, and/or other conditions of the eye). For example, in some embodiments, the system 200 may be configured to emit therapeutic radiation into an eye of a patient such as the eye 100 described with reference to FIGS. 1A and 1B. The therapeutic radiation may selectively damage retinal pigment epithelial (RPE) cells in a diseased portion of the eye. New RPE cells may regenerate to replace damaged RPE cells, which may reduce or eliminate the effect of the macular disease.

In the exterior views of FIGS. 2A and 2B, a device housing 202, a microscope 204, and a head fixation assembly 206 of the system 200 may be visible. The device housing 202 may be positioned apart from the head fixation assembly 206 and may be fixed relative to the head fixation assembly 206. For instance, in some embodiments, the device housing 202 may be secured to a base 210 at a first location. The head fixation assembly 206 may also be secured to the base 210 at a second location. The head fixation assembly 206 may accordingly be fixed relative to the device housing 202. In some embodiments, the head fixation assembly 206 may be secured directly to the device housing 202 or otherwise fixed relative to the device housing 202.

The device housing 202 may surround or partially surround components of the system 200. For instance, the device housing 202 may partially surround the microscope 204. A first portion of the microscope 204 into which a healthcare provider looks may be external to the device housing 202. A second portion of the microscope 204 (e.g., lenses, focus elements, etc.) may be positioned within the device housing 202. The microscope 204 may be positioned in an optical path to allow an operator to view the eye of the patient. Some additional details of the optical path are provided elsewhere herein.

Additionally, the device housing 202 may surround or partially surround an interactive display device assembly. Some additional details of the interactive display device assembly are provided with reference to FIGS. 3 and 4. The interactive display device assembly and the microscope may be fixed within the device housing 202.

The head fixation assembly 206 may be configured to position and to retain a head of the patient relative to the device housing 202. Accordingly, once fixed within the head fixation assembly 206, the head of the patient may be positioned and retained relative to the interactive display device assembly and/or the microscope 204.

In some embodiments, the head fixation assembly 206 may include a jaw portion 212, a forehead rest 214, and a fixing band 216. A jaw of the patient may be placed in the jaw portion 212 and a forehead of the patient may be placed against the forehead rest 214. The fixing band 216 may be placed and tightened around the head to fix the head in the head fixation assembly 206.

Prior to emission of the therapeutic radiation, a diseased portion of the eye may be diagnosed, which is referred to herein as a diagnostic stage. Diagnosis of the diseased portion may be based on a fundus image of the eye. To acquire the fundus image, the head of the patient may be fixed in the head fixation assembly 206. For instance, the patient may place their jaw against the jaw portion 212 and may place their forehead against the forehead rest 214. The fixing band 216 may be placed around the head and tightened to fix the head relative to the head fixation assembly 206.

With the head of the patient fixed in the head fixation assembly 206, a portion of the fundus of the eye may be aligned with the optical path of the system 200 using a target image and a simulation scene. Some additional details of the alignment are provided elsewhere herein. In response to the alignment, the fundus image may be acquired. The fundus image may include a portion of the fundus (e.g., the fundus 130 of FIG. 1A) that may include a diseased portion such as a fundus lesion. Based on the fundus image, the diseased portion may be diagnosed.

The patient may be removed from the head fixation assembly 206 while the diagnosis is performed. For instance, the fundus image may be communicated or provided to a healthcare provider such that the diagnosis may be performed.

In response to the diagnosis of the diseased portion, the patient may return one or more times for administration of the therapeutic radiation, which is referred to herein as a treatment stage or treatment stages. To administer the therapeutic radiation by the system 200, the head of the patient may be re-fixed in the head fixation assembly 206 such that the head may be fixed relative to the device housing 202 and components therein. The portion of the fundus may be re-aligned with the optical path using the same or substantially the same target image and/or simulation scene. The therapeutic radiation may be emitted through a pupil of the eye to treat the diseased portion of the fundus. There may be multiple treatment stages in which the therapeutic radiation is administered. In each of the multiple treatment stages, the portion of the fundus may be re-aligned with the optical path using the same or substantially the same target image and/or simulation scene.

Alignment during the diagnostic stage and the treatment stage(s) of macula disease may be simplified using the target images and/or simulation scene. For example, involvement of a trained healthcare provider may be reduced and/or a patient may be able to perform the alignment or re-alignment without the trained healthcare provider. In some circumstances, diagnosis of the diseased portion may occur while the head of the patient is fixed in the head fixation assembly 206. In these circumstances, the therapeutic radiation may be emitted while the head of the patient is fixed in the head fixation assembly 206.

FIG. 3 is a block diagram of a first example subsystem 300 that may be included in an embodiment of the system 200 of FIGS. 2A and 2B, arranged in accordance with at least one embodiment described herein. The first subsystem 300 is shown in FIG. 3 with the eye 100 of FIGS. 1A-1C. The first subsystem 300 may include a first interactive display device assembly 302. The first interactive display device assembly 302 may be configured for alignment of a portion of the fundus 130 with an optical path 304. For example, the portion of the fundus 130 may be aligned with the optical path 304 during a diagnostic stage and during one or more treatment stages described with reference to FIGS. 2A and 2B.

The first subsystem 300 may include the device housing 202 described with reference to FIGS. 2A and 2B. The first subsystem 300 may be positioned at least partially within the device housing 202. For instance, the first subsystem 300 may include the first interactive display device assembly 302, a therapeutic radiation source 308, and a fundus photography device 310. The first interactive display device assembly 302, the therapeutic radiation source 308, and the fundus photography device 310 may be positioned, at least partially, in the device housing 202. Additionally, the first subsystem 300 may include a lens assembly 312 and a control device 314, which may be external to the device housing 202.

The lens assembly 312 may include a contact lens. The contact lens may be placed on the eye 100 by a healthcare provider during the diagnostic stage and/or the treatment stage(s). The lens assembly 312 may include one or more lenses along with one or more sensors in some embodiments.

The optical path 304 may include a plane or axis along which one or more components are aligned. For instance, the therapeutic radiation source 308, the fundus photography device 310, the first interactive display device assembly 302, or some combination thereof may be aligned along and/or coaxial with the optical path 304. The optical path 304 may extend from the second subsystem 400 through the lens assembly 312 and into the eye 100 following alignment. For example, when the portion of the fundus 130 is aligned with the optical path 304, the therapeutic radiation source 308 may emit therapeutic radiation either directly or indirectly onto the optical path 304 and to the portion of the fundus 130. Similarly, when the portion of the fundus 130 is aligned with the optical path 304, a fundus image of the portion of the fundus may be acquired directly or indirectly by the fundus photography device 310.

The first interactive display device assembly 302 may include a first interactive display device 324 and a control device 314. The first interactive display device 324 may be positioned in the optical path 304 or otherwise in a visual field of the eye 100. For example, with combined reference to FIGS. 2A and 3, when the head of the patient is fixed in the head fixation assembly 206, the patient may be able to look into the device housing 202 and see the first interactive display device 324 or some portion thereof.

Additionally, the first interactive display device 324 may be stationary relative to the device housing 202. Because the first interactive display device 324 may be stationary relative to the device housing 202, the first interactive display device 324 may also be fixed relative to the head fixation assembly 206.

With continued reference to FIGS. 2A and 3, the first interactive display device 324 may be configured to display a simulation scene. The simulation scene may be visible to the patient when the head of the patient is fixed in the head fixation assembly 206. The simulation scene may include one or more target images. The target images may be displayed in the simulation scene such that optical focus by the eye 100 on the target image may align the portion of the fundus 130 in the optical path 304.

One or more characteristics of a target image may be modified by the first interactive display device 324. Modification of the characteristic of the target image may change a physical condition of an eye of the patient. For example, a position of the target image may be modified, which may result in rotation of the eye of the patient. Additionally, or alternatively, a brightness of the target image may be increased or decreased, which may change a diameter of a pupil. Additionally still, a depth of field or sharpness of the target image may be modified, which may change a shape of a lens. Changes to the shape of the lens may change portion of the fundus on which a therapeutic radiation source focuses.

Referring to FIG. 3, the first interactive display device 324 may include any device that may display the simulation scene. For example, the first interactive display device 324 may include a light-emitting diode (LED) device, an organic LED (OLED), a LED screen, a light field display, or another suitable display device.

The first interactive display device 324 may be communicatively coupled to the control device 314. The control device 314 may be configured to receive patient input from the patient. For example, the control device 314 may be touched, moved, pressed, or otherwise configured to receive patient input from the patient. In some embodiments, the first interactive display device 324 may be configured to manipulate the simulation scene and/or the target images in response to the patient input.

A coupling between the control device 314 and the interactive display device 324 may include a direct coupling. For instance, the first interactive display device 324 may receive signals directly from the control device 314 and may process the signals to manipulate the simulation scene. Alternatively, the coupling between the control device 314 and the interactive display device 324 may include an indirect coupling. For instance, the control device 314 may communicate signals to a processor 330 and non-transitory memory 332, which may process the signals and may communicate instructions and/or commands to the first interactive display device 324. The first interactive display device 324 may manipulate the simulation scene in response to the instructions and/or commands.

The control device 314 may include one or more pieces of hardware configured to receive input from the patient. In some embodiments, the control device 314 may include one or more of a microphone, a display, a keyboard, a touch screen, among other hardware devices.

The first interactive display device 324 may be fixed in the device housing 202 relative to the therapeutic radiation source 308 and/or the fundus photography device 310. The therapeutic radiation source 308 may include any laser or optical device such as a micro pulse laser that may be configured to emit or transmit therapeutic radiation. The therapeutic radiation source 308 may be configured to transmit or emit therapeutic radiation through the pupil 106 of the eye 100 to the portion of the fundus 130. The therapeutic radiation may be in a form of a pulse of laser radiation. The therapeutic radiation may be configured to specifically targeting a layer of the retina 112 that includes the RPE cells 122.

Some laser-based ophthalmological surgical systems such as the system 200, may use real-time feedback to detect RPE damage and stop therapeutic radiation automatically based on the feedback prior to excessively damaging the targeted RPE cells 122. In an example embodiment, the therapeutic radiation is administered to the targeted RPE cells 122 in pulses with a pulse duration of between half a microsecond to several microseconds, such as 1.7 microseconds. The administration of the therapeutic radiation may be periodic in some embodiments, with a pulse frequency in a range from 50 hertz (Hz) to 200 Hz (corresponding to a period in a range of 0.02 seconds to 0.005 seconds), such as about 100 Hz (corresponding to a period of 0.01 seconds). For instance, multiple therapeutic radiation pulses, each with a pulse duration of 1.7 microseconds, may be sequentially administered with a pulse frequency of 100 Hz. The administration of pulses may be terminated in response to the feedback indicating a maximum exposure to the therapeutic radiation.

The therapeutic radiation may in some embodiments be generally more effective at treating conditions of the eye at higher exposure levels. However, at a particular level of exposure (e.g., power) to the therapeutic radiation, therapeutic radiation may cause excessive damage to the eye that may result in vision loss. To avoid or reduce the likelihood of vision loss due to excessive exposure to the therapeutic radiation while permitting exposure up to a sufficiently high level to be effective, some embodiments described herein may start administration of the therapeutic radiation at a relatively low exposure that ramps up with each successive pulse until real-time feedback indicates a threshold exposure has been reached. In an example, the first pulse of therapeutic radiation may be at about 50% of a relatively high energy level, such as a maximum energy level. More generally, the first pulse may be at a relatively low energy level, and each successively administered pulse of therapeutic radiation may be increased compared to the preceding pulse. The amount of increase from pulse to pulse may be fixed or variable. For instance, in an example embodiment, the amount of increase from pulse to pulse may be fixed at 5% of the relatively high energy level.

The real-time feedback may measure exposure of the targeted RPE cells to the therapeutic radiation by measuring the formation and/or bursting of microbubbles that form on melanosomes of the targeted RPE cells in response to exposure to the therapeutic radiation. In an example embodiment, the formation and/or bursting of the microbubbles may be measured with optical feedback and/or acoustic feedback. In particular, the targeted RPE cells may reflect and/or emit optical and/or acoustic signals that may vary depending on the presence, absence, and/or characteristics (e.g., size, velocity) of the microbubbles. Excessive exposure to the therapeutic radiation after microbubble formation and RPE damage could damage other retinal structures, which may lead to formation of scotoma on the retina.

In some embodiments, the therapeutic radiation source 308 may be positioned outside of the optical path 304. In these and other embodiments, the first subsystem 300 may include a first optical element 322. The therapeutic radiation source 308 may be reflected into the optical path 304 by the first optical element 322.

The first optical element 322 may include a beam splitter, a dielectric mirror, a partially transmitting mirror, a waveguide, or another optical element. The first optical element 322 may be configured to transmit or reflect a particular wavelength of the therapeutic radiation. Additionally, in the embodiment of FIG. 3, the first optical element 322 may reflect the therapeutic radiation to into the optical path 304. In other embodiments, one or more optical elements, each of which may include a structure substantially similar to the first optical element 322, may be used to reflect the therapeutic radiation into the optical path 304.

In some embodiments, the therapeutic radiation source 308 may be positioned in the optical path 304 and the first interactive display device 324 or the fundus photography device 310 may be positioned outside the optical path 304.

The fundus photography device 310 may be positioned in the device housing 202. The fundus photography device 310 may be configured to capture a fundus image of the portion of the fundus 130 of the eye 100. In some embodiments, the fundus photography device 310 may be configured to communicate the fundus image or data representative thereof such that a healthcare provider may have access to the fundus image.

The fundus photography device 310 may include a fundus camera (e.g., a charge-coupled device (CCD) or a complementary metal-oxide semiconductor (CMOS) image sensors) or a light field camera. The fundus photography device 310 may be fixed within the device housing 202 and used in conjunction with the first interactive display device 324.

In some embodiments, the fundus photography device 310 may be positioned outside the optical path 304. In these and other embodiments, the first subsystem 300 may include a second optical element 318. The fundus image may be reflected from the optical path 304 by the second optical element 318.

The second optical element 318 may include a beam splitter, a dielectric mirror, a waveguide, or another optical element. Additionally, in the embodiment of FIG. 3, the second optical element 322 reflects the fundus image to into the optical path 304. In other embodiments, one or more optical elements may be used to reflect the fundus image into the optical path 304.

The second optical element 318 may include a beam splitter, a dielectric mirror, a partially transmitting mirror, a waveguide, or another optical element. The second optical element 318 may be configured to transmit or reflect a particular wavelength that may be specific to the fundus image. Additionally, in the embodiment of FIG. 3, the second optical element 318 may reflect the fundus image from the optical path 304. In other embodiments, one or more optical elements, each of which may include a structure substantially similar to the second optical element 318, may be used to reflect the fundus image into the optical path 304.

In some embodiments, the fundus photography device 310 may be positioned in the optical path 304. In these and other embodiments, the first interactive display device 324 or the therapeutic radiation source 308 may be positioned outside the optical path 304.

As described above, in a diagnostic stage, the target image may be displayed in the visual field of the patient. The portion of the fundus 130 may be aligned in the optical path 304 by the patient optically focusing on the target image. The fundus photography device 310 may acquire the fundus image following the alignment. Diagnosis of the diseased portion may be based on a fundus image.

After the diagnosis of the diseased portion, the patient may return one or more times for administration of the therapeutic radiation by the therapeutic radiation source 308.

Prior to administration, the portion of the fundus 130 may be re-aligned in the optical path 304 using the same or substantially the same target image and/or simulation scene. The therapeutic radiation may be emitted through a pupil 106 of the eye 100 to treat the diseased portion of the fundus 130. There may be multiple treatment stages in which the therapeutic radiation source 308 administers the therapeutic radiation. In each of the multiple treatment stages, the portion of the fundus 130 may be re-aligned with the optical path 304 using the same or substantially the same target image and/or simulation scene.

Alignment and/or realignment during the diagnostic stage and the treatment stage(s) may be simplified using the first interactive display device 324 to display the target images and/or simulation scene. For example, using the first interactive display device 324, involvement of a trained healthcare provider may be reduced and/or a patient may be able to perform the alignment or re-alignment without the trained healthcare provider.

Figure 4:
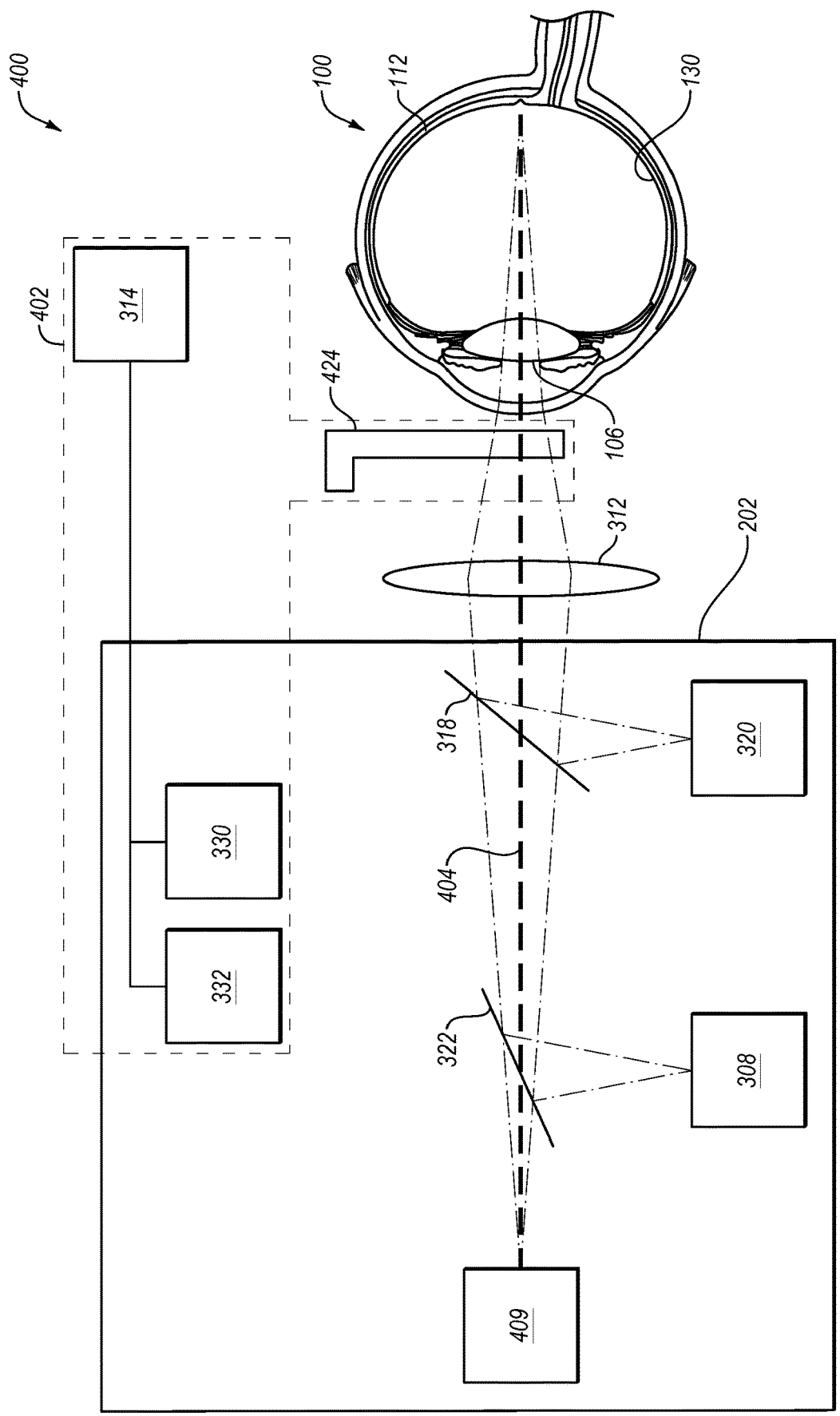
FIG. 4 is a block diagram of a second example subsystem of another embodiment of the system of FIGS. 2A and 2B.

FIG. 4 is a block diagram of a second example subsystem 400 that may be included in an embodiment of the system 200 of FIGS. 2A and 2B arranged in accordance with at least one embodiment described herein. The second subsystem 400 is shown in FIG. 4 with the eye 100 of FIGS. 1A-1C. The second subsystem 400 may include a second interactive display device assembly 402. The second interactive display device assembly 402 may be configured for alignment of a portion of the fundus 130 with an optical path 404. For example, the portion of the fundus 130 may be aligned with the optical path 404 during a diagnostic stage and in one or more treatment stages described with reference to FIGS. 2A and 2B. The optical path 404 may be substantially similar to the optical path 304 described with reference to FIG. 3.

The second subsystem 400 may include one or more components described with reference to FIG. 3. For example, the second subsystem 400 may the therapeutic radiation source 308, the fundus photography device 310, the lens assembly 312, the processor 330, the memory 332, the control device 314, or some combination thereof described with reference to FIG. 4.

The second subsystem 400 or one or more components thereof may be positioned at least partially within the device housing 202 described with reference to FIGS. 2A and 2B. For instance, the second subsystem 400 may include the therapeutic radiation source 308 and the fundus photography device 310, which may be positioned, at least partially, in the device housing 202. Additionally, the second subsystem 400 may include the second interactive display device assembly 402, the lens assembly 312, and the control device 314, which may be external to the device housing 202.

The second interactive display device assembly 402 may include a second interactive display device 424 and the control device 314. The second interactive display device 424 may be placed in the optical path 404 or in a visual field of the eye 100. In particular, in the second subsystem 400, the second interactive display device 424 may include a near-field display device that may project a holographic image into the optical path 404 or the visual field of the eye 100.

For example, with combined reference to FIGS. 2A and 4, when the head of the patient is fixed in the head fixation assembly 206, the second interactive display device 424 may be placed or positioned such that the patient may look through the second interactive display device 424.

With continued reference to FIGS. 2A and 4, the second interactive display device 424 may be configured to display a simulation scene. The simulation scene may be visible to the patient when the head of the patient is fixed in the head fixation assembly 206 and the second interactive display device 424 is placed or positioned in the optical path 404 or the visual field of the eye 100. The simulation scene may include one or more target images. The target images may be displayed in the simulation scene and may include one or more characteristics. Optical focus by the eye 100 on the target image may align the portion of the fundus 130 in the optical path 404, may help focus therapeutic radiation relative to the fundus 130, and may change one or more physical characteristics of the eye 100.

One or more characteristics of a target image may be modified by the second interactive display device 424. Modification of the characteristic of the target image may change a physical condition of an eye of the patient. For example, a position of the target image may be modified, which may result in rotation of the eye of the patient. Additionally, or alternatively, a brightness of the target image may be increased or decreased, which may change a diameter of a pupil. Additionally still, a depth of field or sharpness of the target image may be modified, which may change a shape of a lens. Changes to the shape of the lens may change portion of the fundus on which a therapeutic radiation source focuses.

The second interactive display device 424 may include any device that may display the simulation scene. For example, the second interactive display device 424 may include a light-emitting diode (LED) device, an organic LED (OLED), a LED screen, a light field display, or another suitable display device.

Referring to FIG. 4, the second interactive display device 424 may include any device that may display the simulation scene. For example, the second interactive display device 424 may include a near-field display device, a holographic display device, or another suitable display device. The second interactive display device 424 may be communicatively coupled to the control device 314. The second interactive display device 424 may be configured to manipulate the simulation scene and/or the target images in response to the patient input. The second interactive display device 424 may be directly coupled to the control device 314 or indirectly coupled to the control device 314. For instance, the second interactive display device 424 may be indirectly coupled via the processor 330 and/or the non-transitory memory 332.

The second interactive display device 424 may be fixed in the device housing 202 relative to the therapeutic radiation source 308 and/or the fundus photography device 310. The therapeutic radiation source 308 may be configured to transmit or emit therapeutic radiation through the pupil 106 of the eye 100 to the portion of the fundus 130 as described above.

In some embodiments of the second subsystem 400, the therapeutic radiation source 308 may be positioned outside of the optical path 404. In these and other embodiments, the second subsystem 400 may include the first optical element 322 that may reflect the therapeutic radiation into the optical path 304. In some embodiments of the second subsystem 400, the therapeutic radiation source 308 may be positioned in the optical path 404, which is represented in FIG. 4 by component 409.

In some embodiments of the second subsystem 400, the fundus photography device 310 may be positioned outside the optical path 404. In these and other embodiments, the second subsystem 400 may include the second optical element 318. The fundus image may be reflected from the optical path 404 by the second optical element 318 to the fundus photography device 310. In some embodiments, the fundus photography device 310 may be positioned in the optical path 404, which is represented in FIG. 4 by component 409.

As above, alignment and/or realignment during the diagnostic stage and the treatment stage(s) may be simplified using the second interactive display device 424 to display the target images and/or simulation scene. For example, using the second interactive display device 424, involvement of a trained healthcare provider may be reduced and/or a patient may be able to perform the alignment or re-alignment without the trained healthcare provider.

FIGS. 5A-5G illustrate example changes in optical alignment using an example target image 502 that may be implemented in the system of FIGS. 2A and 2B, arranged in accordance with at least one embodiment described herein. The changes in alignment are depicted between an eye 506 and the target image 502 included in an example simulation scene 504. The eye 506 may be substantially similar to and may correspond to the eye 100 described elsewhere herein.

In FIGS. 5A-5G, the target image 502 may include an aiming reticle. In some embodiments, the target image 502 may include other objects. For example, the target image 502 may include geometric object, one or more letters, a word, a photograph, or some other suitable object.

In FIGS. 5A-5G depict changes to the target image 502 and corresponding changes to the eye 506. The changes to the eye 506 may align the eye 506 in an optical path (e.g., the optical path 304 or 404). The simulation scene 504 is shown in FIGS. 5A-5G as displayed in a visual field of a patient whose head is fixed to a system such as the system 200 of FIGS. 2A and 2B. The eye 506 shown in FIGS. 5A-5G as viewed from the system 200.

Figure 5A:
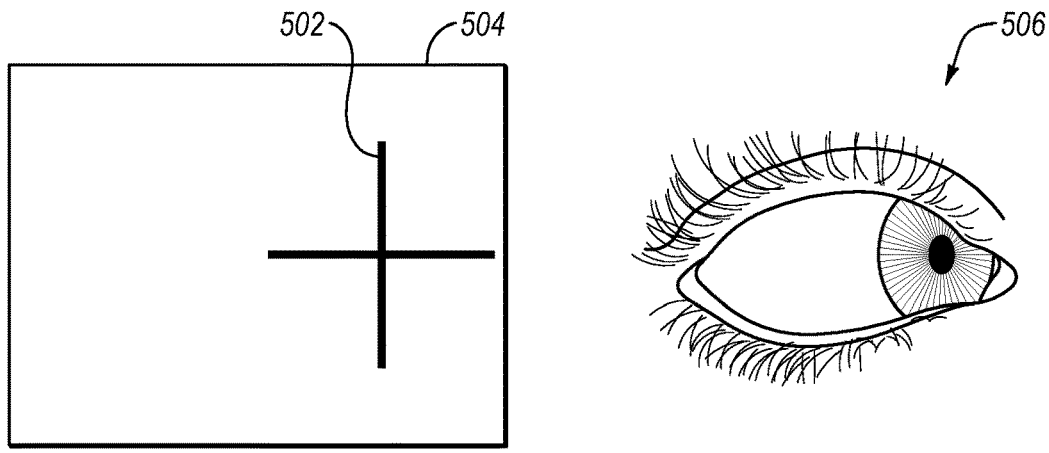
FIGS. 5A-5G illustrate example changes in optical alignment using an example target image that may be implemented in the system of FIGS. 2A and 2B.

In FIG. 5A, the target image 502 may be moved to a left portion of the simulation scene 504. In response, the eye 506 may move to the left side of an orbital socket.

Figure 5B:
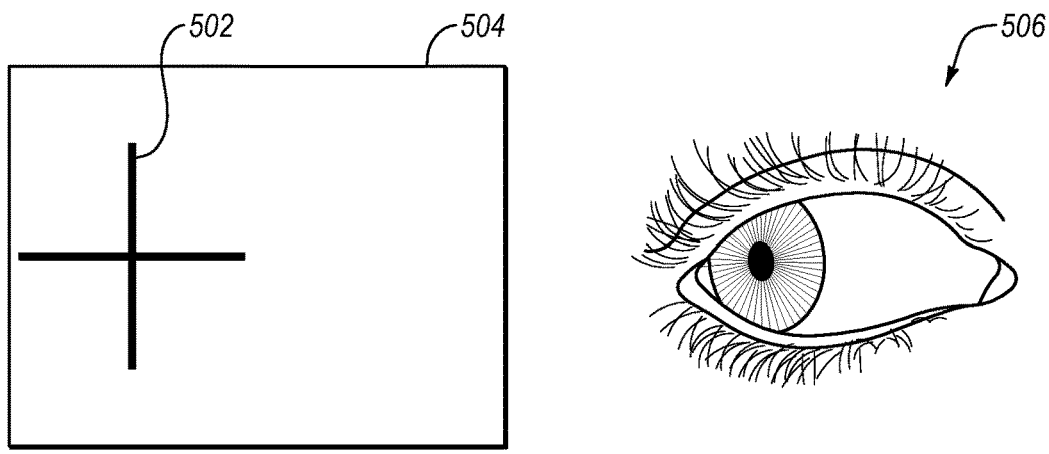
Figure 5C:
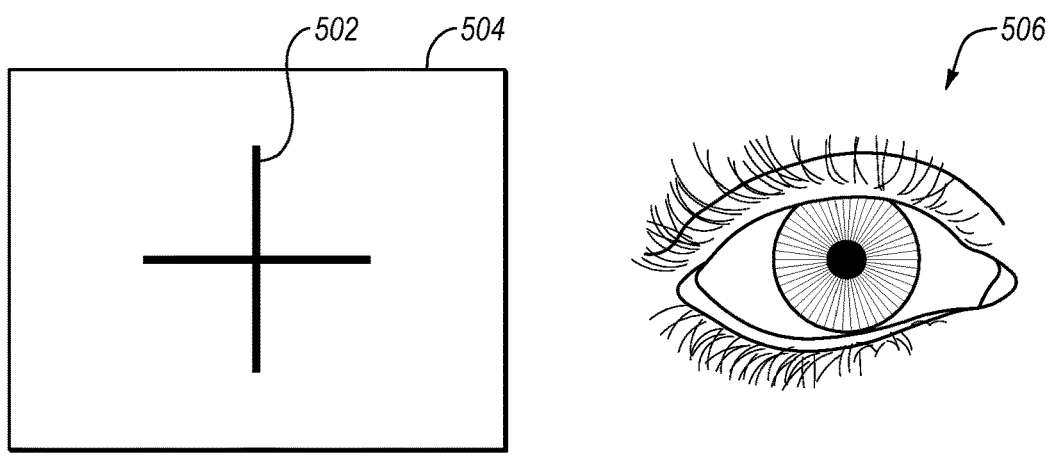

Accordingly, the eye may be converging inward at a particular angle or diverging at a particular angle. In FIG. 5B, the target image 502 may be moved to a right portion of the simulation scene 504. In response, the eye 506 may move to the right side of an orbital socket. Accordingly, the eye 506 may be converging inward at a particular angle or diverging at a particular angle. In FIG. 5C, the target image 502 may be moved to a central portion of the simulation scene 504. In response, the eye 506 may move to a central portion of an orbital socket such that the eye 506. Accordingly, the eye 506 may be look straight forward.

Figure 5D:
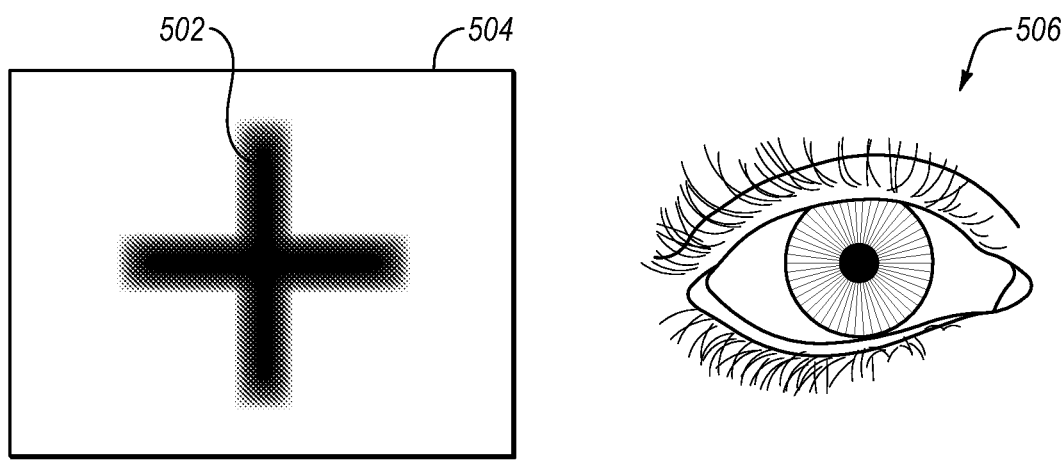

In FIG. 5D, the target image 502 may be depicted at a particular depth of field. For instance, the target image 502 may be depicted out of focus or blurry, which may force the eye 506 to focus on the image. As the eye 506 focuses on the target image 502, the shape of the lens (e.g., the lens 110 of FIG. 1A) may change. Change in the shape of the lens may align the optical path or therapeutic radiation with a particular portion of the fundus (e.g., the lens 110 of FIG. 1A). For example, the particular depth of field of the target image 502 may be configured such that optical focus on the target image 502 by the patient affects an elongation of the lens of the eye 506. The elongation of the lens of the eye 506 may increase or decrease an area of the portion of the fundus affected by the therapeutic radiation.

Additionally, the simulation scene may include multiple target images, which may each be substantially similar to the target image 502. A first of the multiple target images may be displayed such that it appears closer to the patient than a second of the multiple target images. Focusing on the first of the multiple target images or the second of the multiple target images may change the shape of the lens of the eye 506.

Figure 5E:
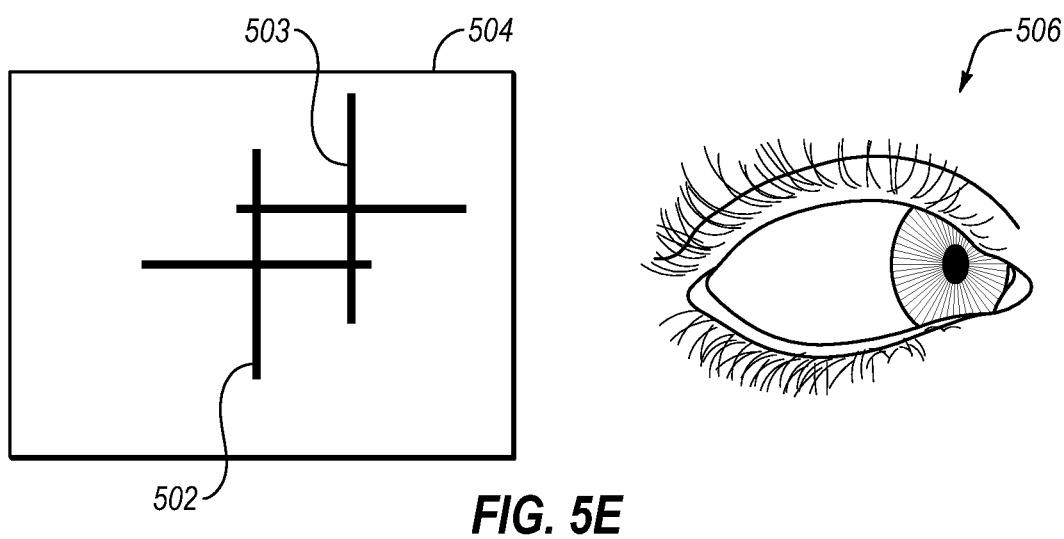

In FIG. 5E, the simulation scene 504 may include the target image 502 and another target image 503. In FIG. 5E, both the target image 502 and the other target image 503 may both be aiming reticles. In other embodiments, the target image 502 and/or the other target image 503 may include other objects. In the simulation scene 504 of FIG. 5E, the other target image 503 may be moved to overlap the target image 502. In response, the eye 506 may move to a central portion of an orbital socket such that the eye 506 is looking straight forward.

Figure 5F:
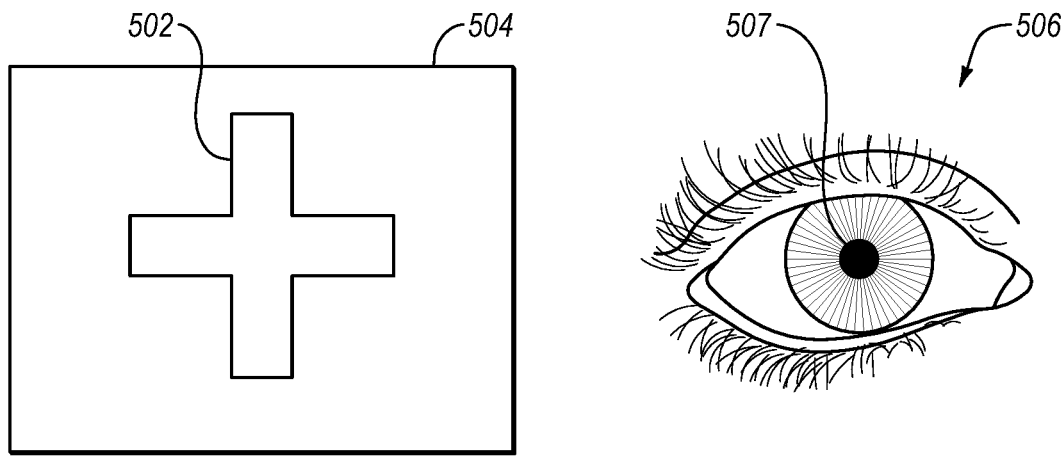
Figure 5G:
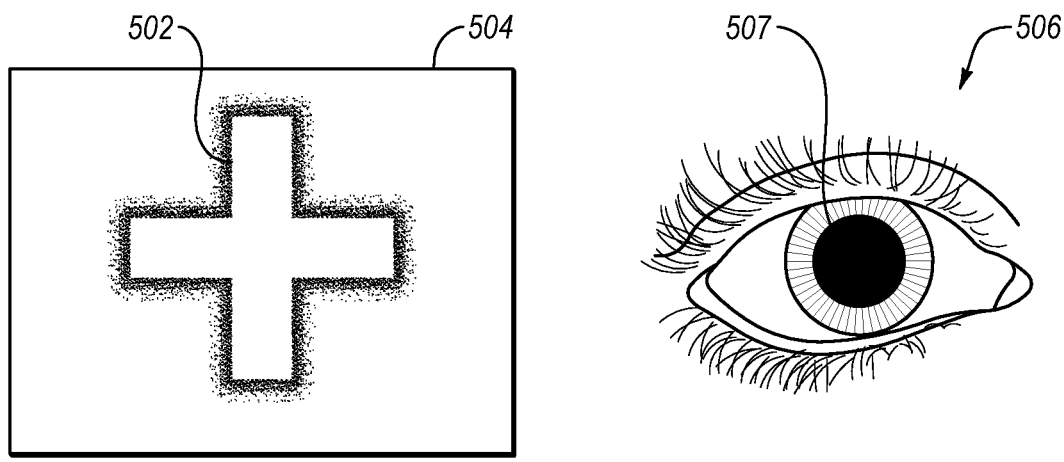

In FIG. 5F, the target image 502 may have a first particular brightness. In response, a pupil 507 of the eye 506 may include a first particular diameter. In FIG. 5G, the target image 502 may have a second particular brightness. In response, a pupil 507 of the eye 506 may include a second particular diameter.

As described above, in a diagnostic stage, the target image 502 of one or more of FIGS. 5A-5G may be displayed in the visual field of the patient. The portion of the fundus 130 may be aligned in the optical path by the patient optically focusing on the target image 502. A fundus photography device (e.g., the fundus photography device 310 of FIGS. 3 and 4) may acquire the fundus image following the alignment.

Diagnosis of the diseased portion may be based on a fundus image.

After the diagnosis of the diseased portion and prior to administration, the target image 502 of one or more of FIGS. 5A-5G may be re-displayed in the visual field of the patient. The portion of the fundus may be re-aligned in the optical path. Following the alignment using the target image 502, the therapeutic radiation may be emitted through a pupil 507 of the eye 506 to treat the diseased portion of the fundus.

Figure 6:
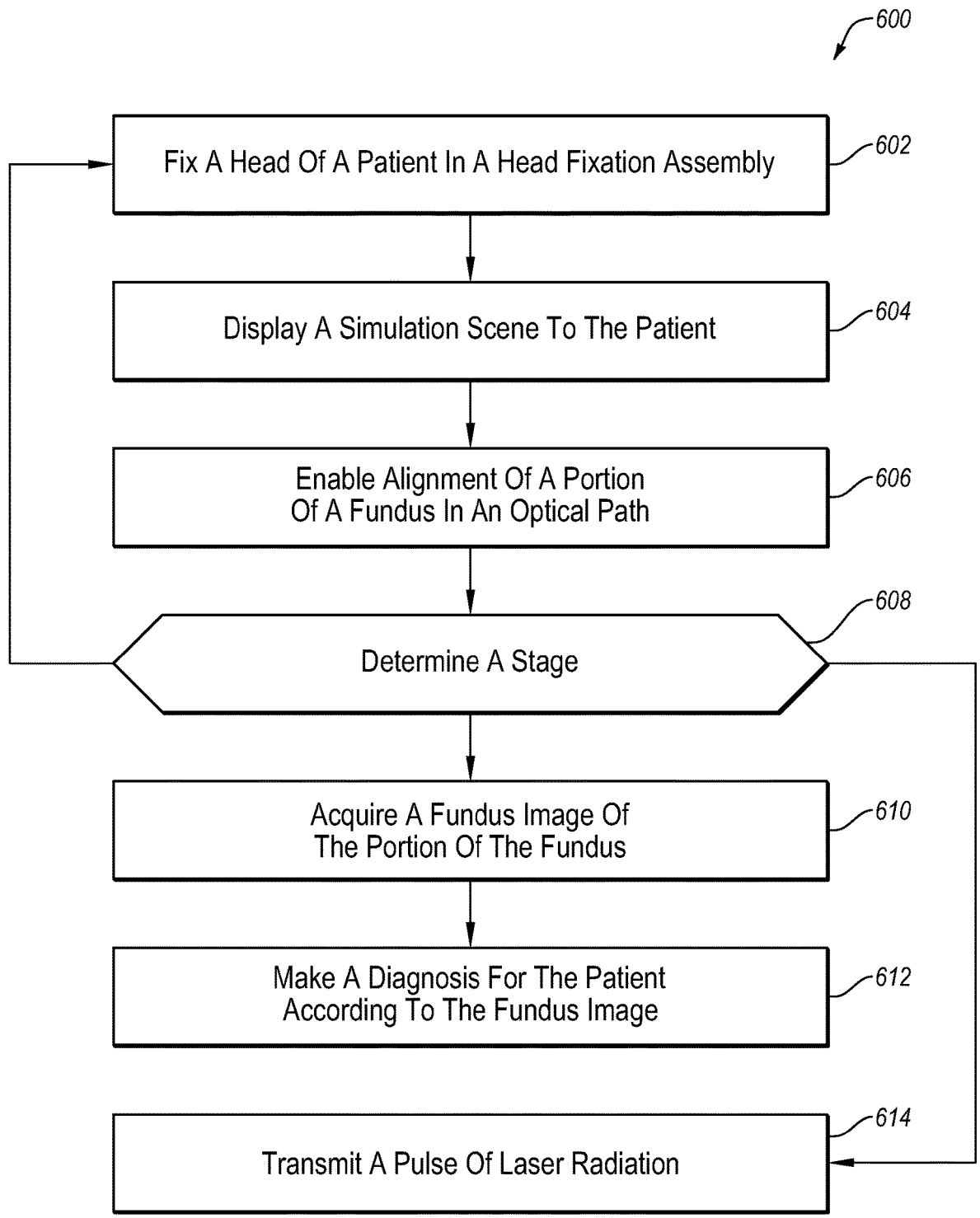
FIG. 6 illustrates a flow diagram of an example method of laser-based ophthalmological surgical treatment.

FIG. 6 illustrates a flow diagram of an example method 600 of laser-based ophthalmological surgical treatment, arranged in accordance with at least some embodiments described herein. The method 600 may be performed, in whole or in part, in the system 200, the subsystems 300 or 400 and/or in other systems and configurations. Alternatively or additionally, the method 600 may be implemented at least partially by a processor device that performs or controls performance of one or more of the operations of the method 600. For instance, a computer (such as the computing device 700 of FIG. 7) or another processor device may be communicatively coupled to the system 200 or the subsystems 300 or 400 and may execute software or other computer-readable instructions accessible to the computer, e.g., stored on a non-transitory computer-readable medium accessible to the computer, to perform or control the system 200 or the subsystems 300 or 400 to perform the method 600 or a portion thereof.

The method 600 may include one or more of blocks 602, 604, 606, 608, 610, 612, and 614. Although illustrated as discrete blocks, various blocks may be divided into additional blocks, supplemented with additional blocks, combined into fewer blocks, or eliminated, depending on the particular implementation. The method 600 may begin at block 602.

In block 602 ("Fix A Head Of A Patient In A Head Fixation Assembly"), a head of a patient may be fixed in a head fixation assembly. The head fixation assembly may include for instance the head fixation assembly 206 of FIGS. 2A and 2B. Block 602 may be followed by block 604.

In block 604 ("Display A Simulation Scene To The Patient"), a simulation scene may be displayed to the patient. The simulation scene may be displayed by an interactive display device fixed relative to the head fixation assembly. In some embodiments, interactive display device may include an LED device, an OLED, a LED screen, a light field display, or a holographic display device. The simulation scene may include a target image. The target image may be included in the simulation scene. The target image may include an aiming reticle in some embodiments. The target image may have a particular depth of field, which may be configured such that optical focus on the target image by the patient affects an elongation of a lens of the eye. Block 604 may be followed by block 606.

In block 606 ("Enable Alignment Of A Portion Of A Fundus Of An Eye In An Optical Path"), alignment of a portion of a fundus of an eye of the patient in an optical path may be enabled. In some embodiments, enabling alignment may include receiving patient input from a control device that is communicatively coupled to the interactive display device. Responsive to the patient input, one or more objects in the simulation scene may be manipulated. In other embodiments, the enabling alignment may include modification of a characteristic of a target image in the simulation scene. Modification of the characteristic of the target image may change a physical condition of an eye of the patient. For example, a position of the target image may be modified, which may result in rotation of the eye of the patient. Additionally or alternatively, a brightness of the target image may be increased or decreased, which may change a diameter of a pupil. Additionally still, a depth of field or sharpness of the target image may be modified, which may change a shape of a lens. Changes to the shape of the lens may change portion of the fundus on which a therapeutic radiation source focuses. The manipulating the one or more objects may include aligning a first object with a second object. For instance, the one or more objects may include a target image and another target image. Alignment of the target image with the other image in the simulation scene may align the portion of the fundus of the eye. When the first object of the one or more objects reaches the target image, a signal may be received from the controller that indicates the patient is optically focused on the target image. Block 606 may be followed by block 608.

In block 608 ("Determine a Stage"), a stage may be determined. For example, it may be determined whether one or more of blocks 602, 604, and 606 are being performed in a diagnostic stage or in a treatment stage. The treatment state may be subsequent to the diagnostic stage. In response to a determination that one or more of blocks 602, 604, and 606 are performed in the diagnostic stage, the method 600 may proceed to block 610. In response to a determination that one or more of blocks 602, 604, and 606 are performed in the treatment stage, the method 600 may proceed to block 614.

In block 610 ("Acquire A Fundus Image Of The Portion Of The Fundus"), a fundus image of the portion of the fundus may be acquired. The fundus image may be acquired responsive to alignment of the portion of the fundus in the optical path. Block 610 may be followed by block 612. In block 612 ("Make A Diagnosis For The Patient According To The Fundus Image"), a diagnosis for the patient may be made according to the fundus image. The making the diagnosis may be performed between the treatment stage and the diagnostic stage. Block 612 may be followed by one or more of blocks 602, 604, 606, and 608.

For example, following the diagnosis in block 612, the method 600 may proceed to block 602. The method 600 may proceed to block 602 in at a subsequent time such as when the patient returns for treatment of a macular disease following diagnosis of the macular disease based on the fundus image. At block 602, the head may be re-fixed in the head fixation assembly. Block 602 may be followed by block 604. At block 604, the simulation scene may be re-displayed to the patient. The simulation scene or at least the target image may be displayed as displayed in the diagnostic stage. Block 604 may be followed by block 606. At block 606, subsequent alignment of the portion of the fundus in the optical path based on optical focus by the patient on the target image may be enabled. Block 606 may be followed by block 608. At block 608 it may be determined that blocks 602, 604, and 606 may be performed in the treatment stage. The method 600 may accordingly proceed to block 614. In block 614 ("Transmit A Pulse Of Laser Radiation"), a pulse of laser radiation may be transmitted. The pulse of laser radiation may be transmitted through a pupil of the patient to the portion of the fundus.

It may be appreciated that, for this and other procedures and methods disclosed herein, the functions performed in the processes and methods may be implemented in differing order. Furthermore, the outlined steps and operations are only provided as examples, and some of the steps and operations may be optional, combined into fewer steps and operations, or expanded into additional steps and operations without detracting from the disclosed embodiments.

Figure 7:
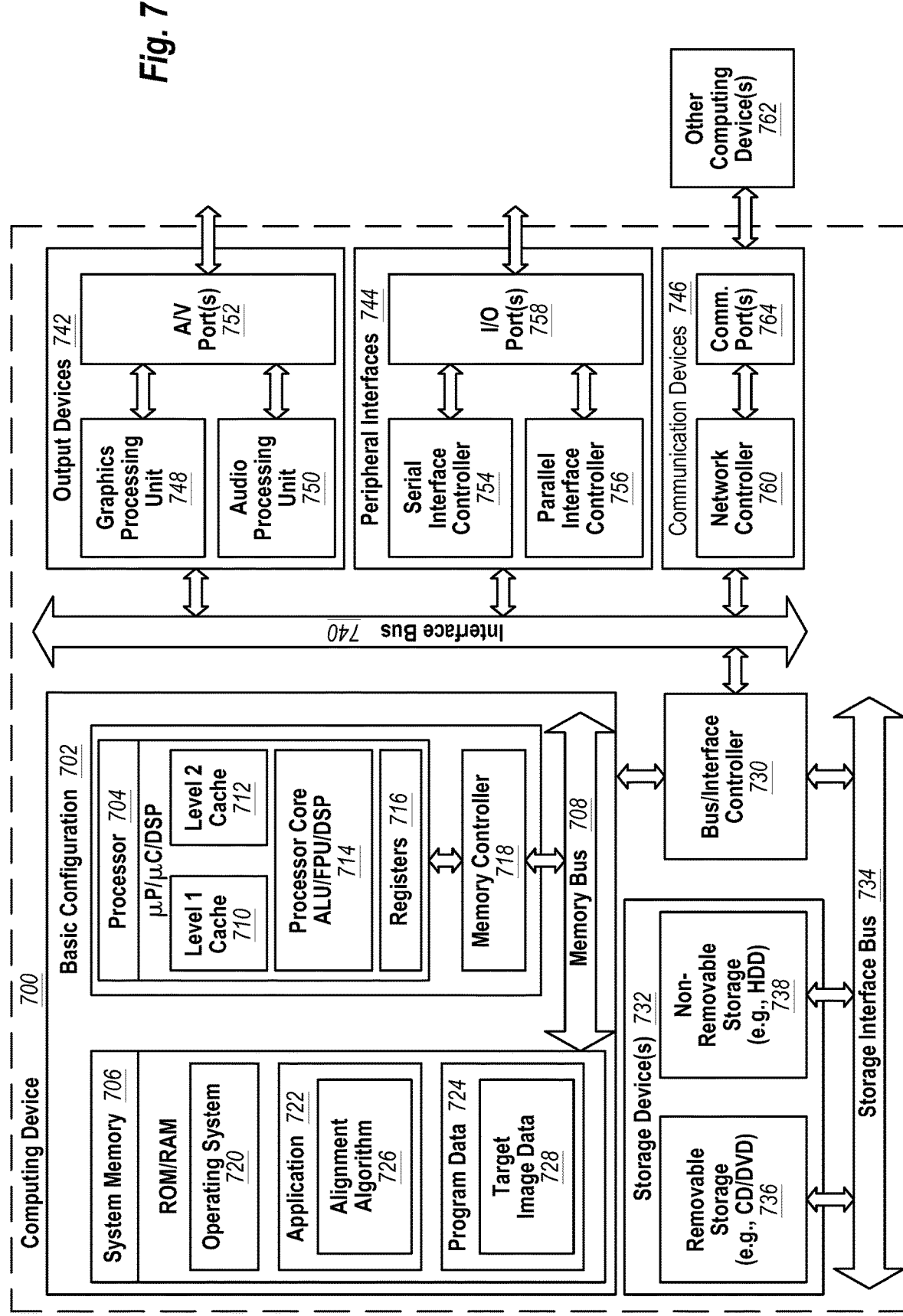
FIG. 7 illustrates a block diagram of an example computing device, all arranged in accordance with at least one embodiment of the present disclosure.

FIG. 7 illustrates a block diagram of an example computing device 700, in accordance with at least one embodiment of the present disclosure. The computing device 700 may be used in some embodiments to perform or control performance of one or more of the methods and/or operations described herein. For instance, the computing device 700 may be communicatively coupled to and/or included in the system 200 of FIG. 2A or 2B to perform or control performance of the method 600 of FIG. 6. In a basic configuration 702, the computing device 700 typically includes one or more processors 704 and a system memory 706. A memory bus 708 may be used for communicating between the processor 704 and the system memory 706.

Depending on the desired configuration, the processor 704 may be of any type including, such as a microprocessor (µP), a microcontroller (µC), a digital signal processor (DSP), or any combination thereof. The processor 704 may include one or more levels of caching, such as a level one cache 710 and a level two cache 712, a processor core 714, and registers 716. The processor core 714 may include an arithmetic logic unit (ALU), a floating point unit (FPU), a digital signal processing core (DSP Core), or any combination thereof. An example memory controller 718 may also be used with the processor 704, or in some implementations, the memory controller 718 may be an internal part of the processor 704.

Depending on the desired configuration, the system memory 706 may be of any type, such as volatile memory (such as RAM), non-volatile memory (such as ROM, flash memory, or the like), or any combination thereof. The system memory 706 may include an operating system 720, one or more applications 722, and program data 724. The application 722 may include an alignment algorithm 726 that is arranged to align a portion of the fundus of an eye with an optical path. The program data 724 may include target image data 728. The target image data 728 may include one or more characteristics of a target image (e.g., the target image 502 of FIGS. 5A-5G). The one or more characteristics may be used to align and/or realign the portion of the fundus in an optical path. The one or more characteristics may include a position, a brightness, a depth of field, sharpness, some combination thereof or some other characteristic of the target image. Additionally, the program data 724 may include information used to relate a particular patient with the target image data 728. In some embodiments, the application 722 may be arranged to operate with the program data 724 on the operating system 720 to perform one or more of the methods and/or operations described herein, including those described with respect to FIG. 6.

The computing device 700 may include additional features or functionality, and additional interfaces to facilitate communications between the basic configuration 702 and any other devices and interfaces. For example, a bus/interface controller 730 may be used to facilitate communications between the basic configuration 702 and one or more data storage devices 732 via a storage interface bus 734. The data storage devices 732 may include removable storage devices 736, non-removable storage devices 738, or a combination thereof. Examples of removable storage and non-removable storage devices include magnetic disk devices such as flexible disk drives and hard-disk drives (HDDs), optical disk drives such as compact disk (CD) drives or digital versatile disk (DVD) drives, solid state drives (SSDs), and tape drives to name a few. Example computer storage media may include volatile and nonvolatile, removable and non-removable media implemented in any method or technology for storage of information, such as computer-readable instructions, data structures, program modules, or other data.

The system memory 706, the removable storage devices 736, and the non-removable storage devices 738 are examples of computer storage media. Computer storage media includes, but is not limited to, RAM, ROM, EEPROM, flash memory or other memory technology, CD-ROM, digital versatile disks (DVDs) or other optical storage, magnetic cassettes, magnetic tape, magnetic disk storage or other magnetic storage devices, or any other medium which may be used to store the desired information and which may be accessed by the computing device 700. Any such computer storage media may be part of the computing device 700.

The computing device 700 may also include an interface bus 740 for facilitating communication from various interface devices (e.g., output devices 742, peripheral interfaces 744, and communication devices 746) to the basic configuration 702 via the bus/interface controller 730. The output devices 742 include a graphics processing unit 748 and an audio processing unit 750, which may be configured to communicate to various external devices such as a display or speakers via one or more A/V ports 752.

The peripheral interfaces 744 include a serial interface controller 754 or a parallel interface controller 756, which may be configured to communicate with external devices such as input devices (e.g., keyboard, mouse, pen, voice input device, touch input device, and/or others), sensors, or other peripheral devices (e.g., printer, scanner, and/or others) via one or more I/O ports 758. The communication devices 746 include a network controller 760, which may be arranged to facilitate communications with one or more other computing devices 762 over a network communication link via one or more communication ports 764.

The network communication link may be one example of a communication media.

Communication media may typically be embodied by computer-readable instructions, data structures, program modules, or other data in a modulated data signal, such as a carrier wave or other transport mechanism, and may include any information delivery media. A "modulated data signal" may be a signal that includes one or more of its characteristics set or changed in such a manner as to encode information in the signal. By way of example, and not limitation, communication media may include wired media such as a wired network or direct-wired connection, and wireless media such as acoustic, radio frequency (RF), microwave, infrared (IR), and other wireless media.

The term "computer-readable media" as used herein may include both storage media and communication media.

The computing device 700 may be implemented as a portion of a small-form factor portable (or mobile) electronic device such as a cell phone, a personal data assistant (PDA), a personal media player device, a wireless webwatch device, a personal headset device, an application-specific device, or a hybrid device that include any of the above functions. The computing device 700 may also be implemented as a personal computer including both laptop computer and non-laptop computer configurations.

The present disclosure is not to be limited in terms of the particular embodiments described herein, which are intended as illustrations of various aspects. Many modifications and variations can be made without departing from its spirit and scope.

Functionally equivalent methods and apparatuses within the scope of the disclosure, in addition to those enumerated herein, are possible from the foregoing descriptions. Such modifications and variations are intended to fall within the scope of this disclosure.

Also, the terminology used herein is for the purpose of describing particular embodiments only, and is not intended to be limiting.

With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity.

In general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation, no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to embodiments containing only one such recitation, even when the same claim includes the introductory phrases "one or more" or "at least one" and indefinite articles such as "a" or "an" (e.g., "a" and/or "an" should be interpreted to mean "at least one" or "one or more"); the same holds true for the use of definite articles used to introduce claim recitations. In addition, even if a specific number of an introduced claim recitation is explicitly recited, those skilled in the art will recognize that such recitation should be interpreted to mean at least the recited number (e.g., the bare recitation of "two recitations," without other modifiers, means at least two recitations, or two or more recitations). Furthermore, in those instances where a convention analogous to "at least one of A, B, and C, etc." is used, in general, such a construction is intended in the sense one having skill in the art would understand the convention (e.g., "a system having at least one of A, B, and C" would include but not be limited to systems that include A alone, B alone, C alone, A and B together, A and C together, B and C together, and/or A, B, and C together, etc.).

In those instances where a convention analogous to "at least one of A, B, or C, etc." is used, in general, such a construction is intended in the sense one having skill in the art would understand the convention (e.g., "a system having at least one of A, B, or C" would include but not be limited to systems that include A alone, B alone, C alone, A and B together, A and C together, B and C together, and/or A, B, and C together, etc.).

It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

In addition, where features or aspects of the disclosure are described in terms of Markush groups, those skilled in the art will recognize that the disclosure is also thereby described in terms of any individual member or subgroup of members of the Markush group.

For any and all purposes, such as in terms of providing a written description, all ranges disclosed herein also encompass any and all possible sub ranges and combinations of sub ranges thereof. Any listed range can be easily recognized as sufficiently describing and enabling the same range being broken down into at least equal halves, thirds, quarters, fifths, tenths, and/or others. As a non-limiting example, each range discussed herein can be readily broken down into a lower third, middle third and upper third, etc.

All language such as "up to," "at least," and the like include the number recited and refer to ranges which can be subsequently broken down into sub ranges as discussed above. Finally, a range includes each individual member. Thus, for example, a group having 1-3 cells refers to groups having 1, 2, or 3 cells. Similarly, a group having 1-5 cells refers to groups having 1, 2, 3, 4, or 5 cells, and so forth.

From the foregoing, various embodiments of the present disclosure have been described herein for purposes of illustration, and various modifications may be made without departing from the scope and spirit of the present disclosure. Accordingly, the various embodiments disclosed herein are not intended to be limiting.

What is claimed is:

1. A method of laser-based ophthalmological surgical treatment, the method comprising:
   in a diagnostic stage:
      fixing a head of a patient in a head fixation assembly that is secured relative to a device housing;
      displaying to the patient a simulation scene that includes a target image within a visual field of a patient, wherein the simulation scene is displayed by an interactive display device fixed relative to the head fixation assembly;

aligning a portion of a fundus of an eye of the patient in an optical path based on optical focus by the patient on the target image;

acquiring a fundus image of the portion of the fundus during alignment of the portion of the fundus with the optical path;

in a treatment stage that is subsequent to the diagnostic stage:

displaying the simulation scene to the patient, wherein the simulation scene includes the target image as displayed during the diagnostic stage;

aligning the portion of the fundus in the optical path based on optical focus by the patient on the target image; and transmitting a pulse of laser radiation through a pupil of the patient to the portion of the fundus.

2. The method of claim 1, further comprising:

receiving patient input from a control device that is communicatively coupled to the interactive display device;

manipulating one or more objects in the simulation scene in response to the patient input; and receiving a signal from a controller that indicates the patient is optically focused on the target image when a first object of the one or more objects reaches the target image.

3. The method of claim 2, further comprising aligning the first object with a second object in the simulation scene by manipulating the one or more objects.

4. The method of claim 1, further comprising providing an aiming reticle with the target image.

5. The method of claim 1, further comprising making a diagnosis for the patient according to the fundus image between the treatment stage and the diagnostic stage.

6. The method of claim 1, further comprising providing the target image with a depth of field such that optical focus on the target image by the patient affects an elongation of a lens of the eye.

7. The method of claim 1, further comprising modifying a characteristic of the target image.

8. The method of claim 1, further comprising modifying a characteristic selected from a position of the target image, a brightness of the target image, or a depth of field of the target image.

9. The method of claim 1, further comprising aligning the portion of the fundus by positioning the eye straight ahead or converging inward at a particular angle.

* * * * *